United States Patent [19]
Schinski

[11] 3,971,650
[45] July 27, 1976

[54] HERBICIDAL N¹-METHOXYCARBONYL-N¹-ALKYL-3,5-DINITRO-N⁴-N⁴-DIALKYLSULFANILAMIDE

[75] Inventor: William L. Schinski, San Rafael, Calif.

[73] Assignee: Chevron Research Company, San Francisco, Calif.

[22] Filed: Dec. 17, 1974

[21] Appl. No.: 533,560

Related U.S. Application Data

[63] Continuation-in-part of Ser. No. 375,304, June 29, 1973, abandoned.

[52] U.S. Cl. .................... 71/103; 71/88; 71/94; 71/95; 260/293.73; 260/326.82; 260/397.7 R
[51] Int. Cl.² .......................................... A01N 9/14
[58] Field of Search ................................ 71/103

[56] References Cited
UNITED STATES PATENTS

| | | | |
|---|---|---|---|
| 3,321,292 | 5/1967 | Soloway | 71/103 |
| 3,367,949 | 2/1968 | Soper | 71/103 |
| 3,377,375 | 4/1968 | Stephens | 260/470 |
| 3,823,008 | 7/1974 | Carpenter et al. | 71/103 |
| 3,849,110 | 11/1974 | Soper et al. | 71/103 |

FOREIGN PATENTS OR APPLICATIONS

| | | |
|---|---|---|
| 2,227,744 | 1/1973 | Germany |

*Primary Examiner*—Joseph Paul Brust
*Attorney, Agent, or Firm*—George F. Magdeburger; Dix A. Newell; Raymond Owyang

[57] ABSTRACT

N¹-methoxycarbonyl-N¹-alkyl-3,5-dinitro-N⁴,N⁴-dialkylsulfanilamides are useful as pre-emergence herbicides for crabgrass, with essentially no herbicidal effects on lawn grasses such as ryegrass and dichondra.

7 Claims, No Drawings

HERBICIDAL $N^1$-METHOXYCARBONYL-$N^1$-ALKYL-3,5-DINITRO-$N^4$-$N^4$-DIALKYLSULFANILAMIDE

CROSS-REFERENCE TO RELATED APPLICATION

This application is a continuation-in-part of application Ser. No. 375,304, filed June 29, 1973 now abandoned, incorporated herein by reference.

DESCRIPTION OF THE PRIOR ART

U.S. Pat. No. 3,367,949, issued Feb. 6, 1968 to Q. F. Soper, discloses the use of 3,5-dinitro-$N^4$,$N^4$-dialkylsulfanilamide compounds as pre-emergence herbicides.

U.S. Pat. No. 3,321,292, issued May 23, 1967 to S. B. Soloway et al, discloses the use of 4-(methylsulfonyl)-2,6-dinitro-N,N-dialkylaniline compounds as herbicides.

German Application No. 2,227,744, published Jan. 4, 1973, discloses herbicidal 4-amino-3,5-dinitrobenzenesulfonamide compounds.

DESCRIPTION OF THE INVENTION

The $N^1$-methoxycarbonyl-$N^1$-alkyl-3,5-dinitro-$N^4$,$N^4$-dialkylsulfanilamides of the invention are represented by Formula (I):

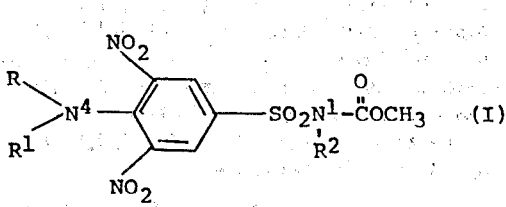

wherein R and $R^1$ individually are cycloalkyl of 3 to 6 carbon atoms or alkyl of 2 to 4 carbon atoms, with the proviso that two alkyl R and $R^1$ groups may together with the nitrogen atom form a 5 to 7 membered heterocyclic ring, and $R^2$ is alkyl of 1 to 3 carbon atoms.

Preferably the total carbon atoms of alkyl R and $R^1$ groups are equal to 5 to 8. The preferred R and $R^1$ groups are alkyl, especially n-alkyl. The preferred $R^2$ group is methyl.

Representative compounds of Formula I are shown in Table I:

TABLE I $N^1$-methoxycarbonyl-$N^1$-methyl-3,5-dinitro-$N^4$,$N^4$-dipropylsulfanilamide $N^1$-methoxycarbonyl-$N^1$-methyl-3,5-dinitro-$N^4$,$N^4$-diisopropylsulfanilamide $N^1$-methoxycarbonyl-$N^1$-methyl-3,5-dinitro-$N^4$,$N^4$-dibutylsulfanilamide $N^1$-methoxycarbonyl-$N^1$-methyl-3,5-dinitro-$N^4$-ethyl-$N^4$-propylsulfanilamide $N^1$-methoxycarbonyl-$N^1$-methyl-3,5-dinitro-$N^4$-propyl-$N^4$-butylsulfanilamide $N^1$-methoxycarbonyl-$N^1$-methyl-3,5-dinitro-$N^4$-isopropyl-$N^4$-sec-butylsulfanilamide $N^1$-methoxycarbonyl-$N^1$-ethyl-3,5-dinitro-$N^4$,$N^4$-dipropylsulfanilamide $N^1$-methoxycarbonyl-$N^1$-ethyl-3,5-dinitro-$N^4$,$N^4$-diisopropylsulfanilamide $N^1$-methoxycarbonyl-$N^1$-ethyl-3,5-dinitro-$N^4$,$N^4$-di-sec-butylsulfanilamide $N^1$-methoxycarbonyl-$N^1$-ethyl-3,5-dinitro-$N^4$-ethyl-$N^4$-propylsulfanilamide $N^1$-methoxycarbonyl-$N^1$-ethyl-3,5-dinitro-$N^4$-ethyl-$N^4$-t-butylsulfanilamide $N^1$-methoxycarbonyl-$N^1$-propyl-3,5-dinitro-$N^4$-ethyl-$N^4$-isopropylsulfanilamide $N^1$-methoxycarbonyl-$N^1$-isopropyl-3,5-dinitro-$N^4$,$N^4$-dipropylsulfanilamide $N^1$-methoxycarbonyl-$N^1$,$N^4$,$N^4$-tripropyl-3,5-dinitrosulfanilamide $N^1$-methoxycarbonyl-$N^1$-methyl-$N^4$,$N^4$-dicyclopropyl-3,5-dinitrosulfanilamide $N^1$-methoxycarbonyl-$N^1$-methyl-$N^4$-cyclopropyl-$N^4$-propyl-3,5-dinitrosulfanilamide $N^1$-methoxycarbonyl-$N^1$-methyl-$N^4$-cyclohexyl-$N^4$-ethyl-3,5-dinitrosulfanilamide $N^1$-methoxycarbonyl-$N^1$-methyl-4-piperidino-3,5-dinitrosulfanilamide $N^1$-methoxycarbonyl-$N^1$-methyl-4-pyrrolidinyl-3,5-dinitrosulfanilamide.

The compounds of the invention are prepared by reaction of an $N^1$-alkyl-3,5-dinitro-$N^4$,$N^4$-dialkylsulfanilamide with methyl chloroformate in the presence of a base to neutralize the hydrogen chloride produced in the reaction, as depicted in equation (1)

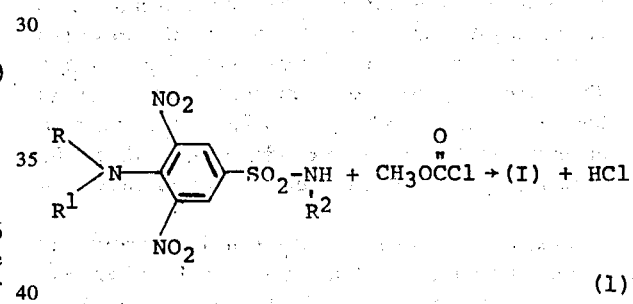

(1)

wherein R, $R^1$ and $R^2$ have the same significance as previously defined.

The reaction (1) is conducted by reacting the sulfanilamide reactant, the alkyl chloroformate and a base in a polar organic solvent. The methyl chloroformate and base are employed in amounts ranging from about 1 to 2 mols per mol of sulfanilamide reactant. Suitable bases include organic amines, such as trialkylamines and pyridine compounds, and inorganic bases such as alkali metal carbonates. The preferred bases are alkali metal carbonates, especially potassium carbonate. Suitable polar organic solvents include oxygenated hydrocarbons such as dialkyl ketones, e.g., acetone and methylethylketone; cycloalkyl ethers, e.g., dioxane and tetrahydrofuran, and acyclic alkyl ethers, e.g., dimethoxyethane, diethylene glycol dimethyl ether and dibutyl ether.

The reaction is conducted at a temperature of from 25° to 100°C, preferably from 35° to 75°C. The reactants are mixed and allowed to react at this temperature from ½ to 24 hours. The reaction is preferably carried out at atmospheric pressure. The reaction product is isolated by conventional methods, such as extraction, filtration or crystallization.

The compounds of the invention may also be prepared by reacting the methyl chloroformate reactant with a 3,5-dinitro-$N^4,N^4$-dialkylsulfanilamide by the same procedure and reaction conditions described for reaction 1. However, this reaction may produce a mixture of $N^1$-methyl-3,5-dinitro-$N^4,N^4$-dialkylsulfanilamide and $N^1$-methoxycarbonyl-3,5-dinitro-$N^4,N^4$-dialkylsulfanilamide.

The compounds of the present invention are, in general, herbicidal in both pre- and post-emergent applications. For pre-emergent control of undesireable vegetation, the compounds will be applied in herbicidal quantities to the environment or growth media of the vegetation, e.g., soil infested with seeds and/or seedlings of such vegetation. Such application will inhibit the growth of or kill the seeds, germinating seeds and seedlings. For post-emergent applications, the compounds of the present invention will be applied directly to the foliage and other plant parts. Generally they are effective against weed grasses as well as broadleaved weeds. However, the compounds are particularly effective as pre-emergent herbicides against certain grasses, e.g., crabgrass.

The compounds of the present invention can be used alone as herbicides. However, it is generally desirable to apply the compounds in herbicidal compositions comprising one or more of the herbicidal compounds intimately admixed with a biologically inert carrier. The carrier may be a liquid diluent or a solid, e.g., in the form of dust, powder or granules. In the herbicidal composition, the active herbicidal compounds can be from about 0.01 to 95% by weight of the entire composition.

Suitable liquid diluent carriers include water and organic solvents, e.g., hydrocarbon such as benzene, toluene, kerosene, diesel oil, fuel oil, and petroleum naphtha. Suitable solid carriers are natural clays such as kaolinite, attapulgite, and montmorillonite. In addition, talcs, pyrophillite, diatomaceous silica, synthetic fine silicas, calcium aluminosilicate and tricalcium phosphate are suitable carriers. Organic materials such as walnut-shell flour, cottonseed hulls, wheat flour, wood flour or redwood-bark flour may also be used as a solid carrier.

The herbicidal composition will also usually contain a minor amount of surface-active agent. Such surface agents are those commonly known as wetting agents, dispersing agents and emulsifying agents, and can be anionic, cationic or nonionic in character. Their herbicidal compositions may also contain other pesticides, adjuvants, stabilizers, conditioners, fillers, and the like.

The amount of herbicidal compound or composition administered will vary with the particular plant part or plant growth medium which is to be contacted, the general location of application — i.e., sheltered areas such as greenhouses, as compared to exposed areas such as fields — as well as the desired type of control. Generally, for both pre- and post-emergent control, the herbicidal compounds of the invention are applied at rates of 0.2 to 60 kg/ha, and the preferred rate is in the range of 0.5 to 40 kg/ha.

EXAMPLES

Example 1

Preparation of
$N^1$-methoxycarbonyl-3,5-dinitro-$N^4,N^4$-di-n-propylsulfanilamide and
$N^1$-methoxycarbonyl-$N^1$-methyl-3,5-dinitro-$N^4,N^4$-di-n-propylsulfanilamide A mixture of 10 g (0.029 mol) 3,5-dinitro-$N^4,N^4$-dipropylsulfanilamide, 2.95 g (0.031 mol) methyl chloroformate, 4.4 g (0.032 mol) potassium carbonate and 250 ml dry acetone was heated at reflux for 4 hours. The inorganic salt was filtered from the reaction mixture. The reaction mixture was then evaporated to given an oily, semi-solid residue. The residue was slurried with boiling benzene. The undissolved solid material (3.6 g) was identified as $N^1$-methoxycarbonyl-3,5-dimitro-$N^4,N^4$-di-n-propylsulfanilamide, m.p. 218°–222°C (dec.). The nuclear magnetic resonance spectrum of this product showed a 3-proton singlet at 3.44 ppm (—OCH$_3$).

Elemental analysis for $C_{14}H_{20}N_4O_8S$ showed: %S, calculated 7.92; and 7.62.

The benzene solution was evaporated and the residue was recrystallized from benzene-hexane to give 5.4 g of $N^1$-methoxycarbonyl-$N^1$-methyl-3,5-dinitro-$N^4,N^4$-di-n-propylsulfanilamide, m.p. 90°–94°C. The nuclear magnetic resonance spectrum of this product showed a 3-proton singlet at 3.39 ppm (—$N^1$—CH$_3$) and a 3-proton singlet at 3.85 ppm (—OCH$_3$).

Elemental analysis for $C_{15}H_{22}N_4O_8S$ showed: %S, calculated 7.66; found 7.90.

Example 2

Preparation of
$N^1$-methoxycarbonyl-$N^1$-methyl-3,5-dinitro-$N^4,N^4$-di-n-propylsulfanilamide.

A mixture of 2.8 g (7.8 mmol) $N^1$-methyl-3,5-dinitro-$N^4$-$N^4$-dipropylsulfanilamide, 0.795 g (8.4 mmol) methyl chloroformate, 1.6 g (8.4 mmol) potassium carbonate and 50 ml dry acetone was heated at reflux for 3 hours. The potassium chloride salt product was filtered and the acetone removed by evaporation under reduced pressure. The residue was extracted with hot benzene. The benzene solution was treated with charcoal, filtered, and evaporated under reduced pressure. The residue was recrystallized from benzene-hexane to give 2.1 g of the product, m.p. 96°–97°C, as an orange solid.

Elemental analysis for $C_{15}H_{22}N_4O_8S$ showed: %C, calculated 43.06; found 43.8. %H, calculated 5.30; found 5.3. %N, calculated 13.39; found 13.9.

Example 3

Preparation of
$N^1$-ethoxycarbonyl-$N^1$-methyl-3,5-dinitro-$N^4,N^4$-di-n-propylsulfanilamide.

A mixture of 3.6 g (0.01 mol) $N^1$methyl-3,5-dinitro-$N^4,N^4$-dipropylsulfanilamide, 2.2 g (0.02 mol) ethyl chloroformate, 2.8 g (0.02 mol) potassium carbonate, and 50 ml dimethoxyethane was heated at reflux until gas evolution ceased. The reaction mixture was filtered and evaporated under reduced pressure. The residue was recrystallized from ethanol to give 2.5 g of the product, m.p. 104°C (dec.).

Elemental analysis for $C_{16}H_{24}N_4O_8S$ showed: %S, calculated 7.42; found 7.6.

Example 4

Preparation of
N-propoxycarbonyl-$N^1$-methyl-3,5-dinitro-$N^4,N^4$-di-n-propylsulfanilamide.

A mixture of 4.5 g (0.0125 mol) $N^1$-methyl-3,5-dinitro-$N^4,N^4$-dipropylsulfanilamide, 3.06 g (0.025 mol) n-propyl chloroformate, 3.5 g (0.025 mol) potassium carbonate, and 75 ml dimethoxyethane was heated at reflux for 2 hours. The reaction mixture was filtered and evaporated under reduced pressure. The residue was recrystallized from ethanol to give 4.5 g of the product, m.p. 110°–113°C, as an orange solid.

Elemental analysis for $C_{17}H_{26}N_4O_8S$ showed: %S, calculated 7.18; found 7.30.

Example 5

Preparation of
$N^1$-butoxycarbonyl-$N^1$-methyl-3,5-dinitro-$N^4,N^4$-di-n-propylsulfanilamide.

A mixture of 4.5 g (0.0125 mol) $N^1$-methyl-3,5-dinitro-$N^4,N^4$-dipropylsulfanilamide, 3.4 g (0.025 mol) n-butyl chloroformate, 3.5 g (0.25 mol) potassium carbonate and 50 ml dimethoxyethane was reacted to produce $N^1$-butoxycarbonyl-$N^1$-methyl-3,5-dinitro-$N^4,N^4$-dipropylsulfanilamide by a procedure similar to that of Example 4. The product was a yellow-orange solid having a melting point of 99°–101°C.

Elemental analysis for $C_{18}H_{28}N_4O_8S$ showed: %S, calculated 7.0; found 7.1.

Example 6

Pre-emergent herbicidal tests of sulfanilamide compounds were made using the following method:

An acetone solution of the test sulfanilamide was prepared by mixing 750 mg sulfanilamide, 220 mg of a nonionic surfactant and 25 ml of acetone. This solution was added to approximately 125 ml of water containing 156 mg of surfactant.

Seeds of the test vegetation were planted in a pot of soil and the solution was sprayed uniformly onto the soil surface at a dose of 3.7 microgram per cm² (gamma/cm²). The pot was watered and placed in a greenhouse. The pot was watered intermittently and was observed for seedling emergence, health of emerging seedlings, etc., for a 3-week period. At the end of this period the herbicidal effectiveness of the solution was rated based on the physiological observations. A 0-to-100 scale was used, 0 representing no phytotoxicity and 100 representing complete kill. The results (average of 3 tests) appear in Table II.

TABLE II

| Compound | Herbicidal Effectiveness | | | |
|---|---|---|---|---|
| | C | R | D | KB |
| $N^1$-methoxycarbonyl-$N^1$-methyl-3,5-dinitro-$N^4,N^4$-di-n-propylsulfanilamide | 90 | 0 | 2 | 7 |
| $N^1$-methoxycarbonyl-3,5-dinitro-$N^4,N^4$-di-n-propylsulfanilamide | 50* | — | — | — |
| $N^1$-ethoxycarbonyl-$N^1$-methyl-3,5-dinitro-$N^4,N^4$-di-n-propylsulfanilamide | 3 | 0 | 0 | 5 |
| $N^1$-propoxycarbonyl-$N^1$-methyl-3,5-dinitro-$N^4,N^4$-di-n-propylsulfanilamide | 0 | 0 | 2 | 2 |
| $N^1$-butoxycarbonyl-$N^1$-methyl-3,5-dinitro-$N^4,N^4$-di-n-propylsulfanilamide | 13 | 0 | 0 | 0 |

*Dosage was 33 gamma/cm² rather than 3.7 gamma/cm²
C = Crabgrass (*Digitaria sanguinalis*)
R = Ryegrass (*Lolium prenne*)
D = Dichondra (*Dichondra repens*)
KB = Kentucky Bluegrass (*Poa pratensis*)

From the data in Table II, it is noted that the $N^1$-methoxy-carbonyl-$N^1$-methyl-3,5-dinitro-$N^4,N^4$-dialkylsulfanilamide provides very selective control of crabgrass without affecting other grasses. This selective control of crabgrass makes the compounds of the invention particularly useful as herbicides for established lawns and turfs.

Example 7

Pre-emergent comparison herbicidal tests between $N^1$-methoxycarboyl-$N^1$-methyl-3,5-dinitro-$N^4,N^4$-di-n-propyl sulfanilamide and two 3,5-dinitro-$N^4,N^4$-dialkylsulfanilamides of U.S. Pat. No. 3,367,949 were conducted by the procedure of Example 6. The results appear in Table III.

TABLE III

| Compound | Dosage Gamma/cm² | Herbicidal Effectiveness | | | |
|---|---|---|---|---|---|
| | | Weed Species Crabgrass | Turfgrass Species | | |
| | | | Bentgrass | Ryegrass | Dichondra |
| $N^1$-methoxycarbonyl-$N^1$-methyl-3,5-dinitro-$N^4,N^4$-di-n-propyl-sulfanilamide | 3.7 | 87 | 17 | 12 | 5 |
| | 1.2 | 45 | 3 | 0 | 5 |
| 3,5-dinitro-$N^4,N^4$-di-n-propyl sulfanilamide | 3.7 | 100 | 94 | 73 | 100 |
| | 1.2 | 78 | 63 | 35 | 63 |
| 3,5-dinitro-$N^4,N^4$-diethyl-sulfanilamide | 3.7 | 8 | 77 | 35 | 95 |
| | 1.2 | 5 | 7 | 0 | 50 |

Example 8

The safety of $N^1$-methoxycarbonyl-$N^1$-methyl-3,5-dinitro-$N^4$, $N^4$-di-n-propylsulfanilamide on crops was tested by the procedure of Example 6. The results appear in Table IV.

TABLE IV

| Dosage Gamma/cm² | Herbicidal Effectiveness | | | | | | | | |
|---|---|---|---|---|---|---|---|---|---|
| | Sweet Corn | Wheat | Oats | Sorghum | Rice | Peas | Cotton | Sugar Beets | Alfalfa |
| 11 | 0 | 7 | 0 | 43 | 7 | 0 | 0 | 0 | 0 |
| 3.7 | 9 | 3 | 0 | 7 | 10 | 0 | 0 | 0 | 3 |
| 1.2 | 0 | 0 | 0 | 7 | 2 | 0 | 0 | 0 | 0 |

Example 9

$N^1$-methyl-3,5-dinitro-$N^4,N^4$-diethylsulfanilamide of U.S. Pat. No. 3,367,949 was tested for the control of crabgrass by the procedure of Example 6. The compound gave a phytotoxicity rating of 17 at a dosage of 3.7 gamma/cm².

What is claimed is:

1. A herbicidal composition for the selective control of crabgrass which comprises a herbicidally effective amount of the compound of the formula

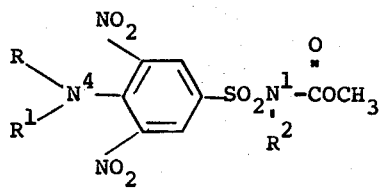

(1)

wherein R and $R^1$ individually are cycloalkyl of 3 to 6 carbon atoms or alkyl of 2 to 4 carbon atoms and $R^2$ is alkyl of 1 to 3 carbon atoms, and a biologically inert carrier.

2. The composition of claim 1 wherein R and $R^1$ are n-alkyl and the total number of carbon atoms of R and $R^1$ are equal to 5 to 8.

3. The composition of claim 2 wherein R and $R^1$ and n-propyl and $R^2$ is methyl.

4. A method for the selective control of crabgrass which comprises applying a herbicidally effective amount of the compound of claim 1 to the growth medium of crabgrass.

5. The method of claim 4 wherein R and $R^1$ are n-alkyl and the total number of carbon atoms of R and $R^1$ are equal to 5 to 8.

6. The method of claim 5 wherein R and $R^1$ are n-propyl and $R^2$ is methyl.

7. The method of claim 4 which comprises applying a herbicidally effective amount of the compound to established lawn grasses.

* * * * *

UNITED STATES PATENT AND TRADEMARK OFFICE
CERTIFICATE OF CORRECTION

PATENT NO. : 3,971,650
DATED : July 27, 1976
INVENTOR(S) : William L. Schinski

It is certified that error appears in the above-identified patent and that said Letters Patent are hereby corrected as shown below:

Col. 3, line 6, should read --ture of $N^1$-methoxycarbonyl-$N^1$-methyl-3,5-dinitro-$N^4$,$N^4$-dialkylsulfanila--.

Signed and Sealed this

Twenty-third Day of November 1976

[SEAL]

Attest:

RUTH C. MASON
Attesting Officer

C. MARSHALL DANN
Commissioner of Patents and Trademarks